United States Patent [19]

Faggian et al.

[11] Patent Number: 5,047,580

[45] Date of Patent: Sep. 10, 1991

[54] PROCESS FOR THE SEPARATION OF SULFURIC ACID FROM AQUEOUS MIXTURES OF PARAFFIN-SULFONIC ACIDS

[75] Inventors: Lucio Faggian, San Donato Milanese; Enrico Borgarello, Turin; Cosimo Franco, Locri; Gerardo Carrillo, San Donato Milanese, all of Italy

[73] Assignees: Eniricerche S.p.A., Milan; Enichem Augusta S.p.A., Palermo, both of Italy

[21] Appl. No.: 498,443

[22] Filed: Mar. 22, 1990

Related U.S. Application Data

[63] Continuation of Ser. No. 136,559, Dec. 22, 1987, abandoned.

[30] Foreign Application Priority Data

Dec. 23, 1986 [IT] Italy ............................... 22815 A/86

[51] Int. Cl.$^5$ ...................... B01D 3/10; C07C 303/42
[52] U.S. Cl. ..................................... 562/33; 562/124; 203/33; 203/36; 203/91; 203/43
[58] Field of Search ...................... 203/43, 46, 33, 36, 203/35, 37, 91; 260/504 S, 513 R, 504 R, 513 T; 423/531; 562/33, 124, 121

[56] References Cited

U.S. PATENT DOCUMENTS

| | | | |
|---|---|---|---|
| 2,223,194 | 11/1940 | Thompson | 260/504 S |
| 2,530,757 | 11/1950 | Bransky et al. | 260/504 S |
| 2,556,256 | 6/1951 | Cone et al. | 260/504 S |
| 3,423,454 | 1/1969 | Marrian | 260/513 R |
| 3,960,938 | 1/1976 | Shuttleworth | 260/504 S |
| 4,178,307 | 12/1979 | Boy et al. | 260/513 R |
| 4,321,214 | 3/1982 | Nicolet | 260/504 R |
| 4,680,147 | 7/1987 | Pistorius | 260/504 S |

FOREIGN PATENT DOCUMENTS

| | | | |
|---|---|---|---|
| 343530 | 2/1931 | United Kingdom | 260/504 S |
| 699341 | 11/1953 | United Kingdom | 260/504 S |

*Primary Examiner*—Wilbur Bascomb, Jr.
*Attorney, Agent, or Firm*—Morgan & Finnegan

[57] ABSTRACT

The purpose of the process of the present invention is to remove excess sulfuric acid from a mixture of paraffin-sulfonic acids free or substantially free, from paraffins.

In order to remove said sulfuric acid, according to the process of the present invention, the paraffin-sulfonic acid mixture is mixed with one or more halogenated solvent(s), possibly in mixture with sulfuric acid to form a two phase mixture consisting of an organic phase containing paraffin-sulfonic acids dissolved therein and an aqueous phase substantially containing sulfuric acid. The organic phase is then treated with sulfuric acid and the organic phase and aqueous phase are then separated and the organic phase is submitted to evaporation, for the removal of the halogenated solvent(s), and with the concentrated paraffin-sulfonic acids being obtained.

13 Claims, No Drawings

PROCESS FOR THE SEPARATION OF SULFURIC ACID FROM AQUEOUS MIXTURES OF PARAFFIN-SULFONIC ACIDS

This is a continuation of co-pending application Ser. No. 07/136,559, filed on 12/22/87, now abandoned.

BACKGROUND OF THE INVENTION

The present invention relates to a process for the separation of sulfuric acid ($H_2SO_4$) from aqueous mixtures of paraffin-sulfonic acids.

SUMMARY OF THE INVENTION

The present invention is a process for removing sulfuric acid ($H_2SO_4$) from a paraffin-sulfonic solution. The process comprises (a) admixing with the paraffin sulfonic solution at least one halogenated solvent selected from the group consisting of methane, ethane, and ethylene halogenated derivatives of the following formulas:

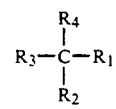  (1)

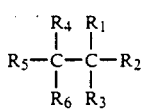  (2)

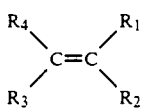  (3)

wherein $R_1$, $R_2$, $R_3$, $R_4$, $R_5$ and $R_6$, each independently, is halogen or hydrogen, with at least one of $R_1$, $R_2$, $R_3$, $R_4$ is halogen, at a temperature of from 10° of an to 80° C., thereby forming a two-phase mixture consisting of an organic phase containing paraffin-sulfonic acids dissolved therein and an aqueous phase substantially containing sulfuric acid;

(b) separating the organic phase from the aqueous phase;

(c) optionally admixing the organic phase with sulfuric acid, thereby forming a two phase mixture consisting of an organic phase containing paraffin-sulfonic acids dissolved therein and an aqueous phase substantially containing sulfuric acid, separating the organic phase from the aqueous phase, and (d) removing the halogenated solvents from the separated organic phase.

The object of the present invention is to provide a process to remove excess $H_2SO_4$ from a refined mixture of paraffin-sulfonic acids free or substantially free, from paraffins.

The residual mixtures from which $H_2SO_4$ must be separated according to the present invention are those which derive from the sulfoxidation of ($C_{12}$–$C_{18}$)-n-paraffin with sulfur dioxide ($SO_2$) and oxygen ($O_2$) in the presence of water ($H_2O$) and ultra-violet light, at a temperature between 25° to 50° C. These residual mixtures undergo one of the following extraction treatments after the removal of n-paraffins (which separate spontaneously) and excess $SO_2$.

a) The residual mixture is dehydrated until the residual mixture becomes cloudy (due to the formation of a two phase system). The cloudy mixture or the supernatant phase of the two phase system is then extracted with $CO_2$ under supercritical conditions to separate the non-sulfoxidated paraffins from the dehydrated residual mixture at a temperature between 32° to 80° C., a pressure between 75 to 350 bars, and with a $CO_2$ to paraffin-sulfonic acids weight ratio of 1/1 to 50/1 so as to obtain a refined mixture.

b) $H_2SO_4$ is added to the residual mixture until at least the residual mixture becomes cloudy (due to the formation of a two-phase system). The cloudy mixture or the supernatant phase of the two phase system is then extracted with $CO_2$ under supercritical conditions, to separate the residual paraffins from the residual mixture at a temperature between 32° to 80° C., a pressure between 75 to 350 bars, and with a $CO_2$ to paraffin-sulfonic acids weight ratio of 1/1 to 50/1 so as to obtain a refined mixture.

c) An aliphatic alcohol containing a number of carbon atoms up to about 4, preferably isopropanol, is added to the residual mixture until a two phase system is formed. The two phase system is then extracted with $CO_2$ under supercritical conditions to separate the residual paraffins from the mixture at a temperature between 32° to 80° C., a pressure between 75 to 350 bars and with a $CO_2$ to paraffin-sulfonic acids weight ratio of from 1/1 to 50/1 so as to obtain a refined mixture.

The refined mixture of paraffin-sulfonic acids free, or substantially free, from paraffins, obtained by means of the above treatments still contains, besides the paraffin-sulfonic acids, a considerable amount of $H_2SO_4$.

The composition of the refined mixtures of paraffin-sulfonic acids obtained by the above methods, i.e., (a) to (c), are the following:

1) ($C_{12}$–$C_{18}$)-Paraffin-sulfonic acids: from 3 to 83% by weight;
2) $H_2O$: from 79 to 8.5% by weight;
3) $H_2SO_4$, from 18 to 8.5% by weight and
4) ($C_{12}$–$C_{18}$)-Paraffins: less than 1% by weight, relative to the weight of ($C_{12}$–$C_{18}$) paraffin-sulfonic acids The starting mixture, even if it is obtained in the above three ways, i.e., (a) to (c), can be obtained in other ways too, so that the present invention should not be considered as being limited to the way in which the starting mixture with the above reported composition is obtained. The process of the invention can be applied to any mixtures, in whatever way they are obtained, having the above compositions.

DETAILED DESCRIPTION OF THE INVENTION

The process is carried out at a temperature between 10° to 80° C., preferably between 20° to 50°. The refined mixture of paraffin-sulfonic acids is mixed with one or more of the above halogenated solvents.

In the two phase mixture, which is formed, the aqueous phase constitutes $H_2SO_4$ and $H_2O$ and the residual refined phase contains paraffin-sulfonic acids dissolved therein. The residual refined phase is separated from the aqueous phase. Optionally it is mixed with $H_2SO_4$ ranging from an aqueous $H_2SO_4$ having a minimum concentration of 70% by weight of $H_2SO_4$ to concentrated $H_2SO_4$, or oleum, or even $SO_3$, at a temperature between 10° C. to 80° C., preferably between 20° C. to 50° C., in such a way that a second phase is formed. The second phase, which constitutes $H_2SO_4$ and $H_2O$, is then separated from the residual refined phase. The halogenated solvent is separated from the residual refined phase. In particular, the separation is carried out by distillation at a temperature below 100° C., preferably lower than 60° C., and more preferably at least partially under vacuum.

Among the halogenated solvents preferred are methylene chloride, chloroform, carbon tetrachloride and dichloroethane. The amount of halogenated solvent(s) added depends on the type of solvent used and the composition of the refined mixture of paraffin-sulfonic acids. The amount used should make it possible to separate the largest amount of $H_2SO_4$ possible.

The amount of $H_2SO_4$ optionally added can be, in the case of 96% concentrated $H_2SO_4$, up to 200% by weight, preferably from 50% to 150% by weight, relative to the weight of the paraffin-sulfonic acids contained in the refined mixture.

A practical embodiment of the process of the present invention is to mix the halogenated solvent(s) and $H_2SO_4$ simultaneously with the refined mixture of paraffin-sulfonic acids in a single processing step.

If any residual $H_2SO_4$ is present before the application of the process according to the present invention, can be removed by being converted into an insoluble product by means of the addition of carbonates, hydroxides or oxides of alkaline-earth metals, particularly, by calcium carbonate, calcium hydroxide or calcium oxide.

Some examples are now given for the purpose of better illustrating the invention. It is understood that the invention is not to be limited to or by the Examples.

EXAMPLE 1

The upper-phase of a raw mixture (from which Decantable n-paraffins and $SO_2$ have been removed) of paraffin-sulfonic acids obtained by sulfoxidation of $(C_{12}-C_{18})$ n-paraffins, and having the following composition:

Paraffin-sulfonic acids: 24.74% by weight
$(C_{12}-C_{18})$-n-paraffins: 26.46% by weight
$H_2O$: 40.94% by weight
$H_2SO_4$: 7.86% by weight was extracted with $CO_2$ under supercritical conditions, so as to separate the residual paraffins after the addition of 20% by weight of $H_2SO_4$ at 96% by weight, referred to the weight of said raw mixture.

The upper phase of the raw mixture was extracted with $CO_2$ under the following conditions:
$CO_2$/paraffinsulfonic acid ratio: 15.5
Extraction pressure: 150 bar
Extraction temperature: 45° C.
Extraction time: 1 hour Analysis of the upper phase of the paraffin-sulfonic acids after extraction showed the following composition:

Paraffinsulfonic acids: 59.95% by weight
$(C_{12}-C_{18})$-n-paraffins: 0.22% by weight
$H_2O$: 28.73% by weight
$H_2SO_4$: 11.11% by weight Then 20.47 g of the upper phase after extraction was mixed with 30.69 g of $CH_2Cl_2$ (methylchloride) in a tightly sealed glass separator funnel.

The separator funnel was thoroughly shaken for a few minutes, and two phases were allowed to separate. After 3 hours of standing at 22° C., the two separated phases were taken away from each other, and analyzed. The lower phase was constituted of:

$H_2O$: 55.44% by weight
$H_2SO_4$: 44.02% by weight
$CH_2Cl_2$: traces

In the upper phase, all charged paraffin-sulfonic acids were present, together with minor amounts of $H_2O$, $H_2SO_4$, n-paraffins, and $CH_2Cl_2$. In particular, the content of $H_2SO_4$, as referred to the present paraffin-sulfonic acids, decreased from 18.5% by weight (before the treatment with $CH_2Cl_2$) to 8.36% by weight. Also the $H_2O$ content, still referred to paraffin-sulfonic acids, decreased from 47.9% by weight to 31.7% by weight.

Aliquots of the upper phase, obtained by means of the treatment with $CH_2Cl_2$, had the composition of:

Paraffin-sulfonic acids: 25.92% by weight
$(C_{12}-C_{18})$-n-paraffins: 0.094% by weight
$H_2O$: 8.21% by weight
$H_2SO_4$: 2.168% by weight
$CH_2Cl_2$: the balance to 100 were extracted, inside a separator funnel, with different amounts of $H_2SO_4$ at 96% by weight to form a lower phase at 22° C. The lower phase was constituted by $H_2SO_4$ and $H_2O$ and separated from the upper phase.

The values obtained for each phase are reported in Table 1.

TABLE 1

| Test No. | $CH_2Cl_2$ Phase Charge, g | Added $H_2SO_4$ at 96%, g | Added $H_2SO_4$/paraffin-sulphonic acids % ratio, by weight | Analysis of the upper phase | | | Analysis of the lower phase | | | $H_2SO_4$/paraffin-sulphonic acids ratio in the upper phase, % by weight | $H_2O$/paraffin-sulphonic acids ratio in the upper phase, % by weight |
| | | | | Paraffin-sulphonic acids, % by weight | $H_2O$, % by weight | $H_2SO_4$, % by weight | Paraffin-sulphonic acids, % by weight | $H_2O$, % by weight | $H_2SO_4$, % by weight | | |
| --- | --- | --- | --- | --- | --- | --- | --- | --- | --- | --- | --- |
| 1.1 | 10.2143 | 1.0944 | 41.33 | 28.64 | 2.74 | 1.364 | 0 | 35.28 | 63.64 | 4.76 | 9.57 |
| 1.2 | 10.3137 | 1.5468 | 57.87 | 28.51 | 1.94 | 1.268 | 0 | 30.37 | 68.69 | 4.45 | 6.80 |
| 1.3 | 10.6545 | 2.0810 | 75.3 | 29.91 | 1.46 | 1.292 | 0 | 27.50 | 71.08 | 4.14 | 4.88 |

EXAMPLE 2

217.8 g of the upper phase mixture of paraffin-sulfonic acids after extraction as in Example 1, was mixed with 652.9 g of $CH_2Cl_2$ in a tightly sealed separator funnel. The separator funnel was thoroughly shaken and two phases were allowed to separate. After standing 24 hours at 22° C., the two separated phases were taken away from each other, and analyzed.

The lower phase was constituted by:

$H_2O$: 50.73% by weight
$H_2SO_4$: 44.03% by weight
$CH_2Cl_2$: small amount

In the upper phase, all charged paraffin-sulfonic acids were present, together with minor amounts of $H_2O$, $H_2SO_4$, n-paraffins and $CH_2Cl_2$. In particular, the content of $H_2SO_4$, referred to the present paraffin-sulfonic acids, decreased from 18.5% by weight (before the treatment with $CH_2Cl_2$) to 7.49% by weight. Also the $H_2O$ content, still referred to the present paraffin-sulfonic acids, decreased from 47.9% by weight to 30.0% by weight.

Aliquots of the upper phase, obtained by means of the treatment with $CH_2Cl_2$, had the composition of:
Paraffin-sulfonic acids: 16.535% by weight
($C_{12}$–$C_{18}$)-n-paraffins: 0.060% by weight
$H_2O$: 4.96% by weight
$H_2SO_4$: 1.238% by weight
$CH_2Cl_2$: the balance to 100 were extracted inside a separator funnel, with different amounts of $H_2SO_4$ at 96% by weight at 22° C., to form a second phase or lower phase. The lower phase was constituted by $H_2SO_4$ and $H_2O$ and separated from the upper phase. The values obtained for each phase are reported in Table 2.

TABLE 2

| Test No. | $CH_2Cl_2$ Phase Charge, g | Added $H_2SO_4$ at 96%, g | Added $H_2SO_4$/paraffin-sulphonic acids % ratio, by weight | Analysis of the upper phase | | | Analysis of the lower phase | | | $H_2SO_4$/paraffin-sulphonic acids ratio in the upper phase, % by weight | $H_2O$/paraffin-sulphonic acids ratio in the upper phase, % by weight |
| --- | --- | --- | --- | --- | --- | --- | --- | --- | --- | --- | --- |
| | | | | Paraffin-sulphonic acids, % by weight | $H_2O$, % by weight | $H_2SO_4$, % by weight | Paraffin-sulphonic acids, % by weight | $H_2O$, % by weight | $H_2SO_4$, % by weight | | |
| 2.1 | 23.8090 | 3.5494 | 90.2 | 16.60 | 0.499 | 0.496 | 0 | 24.41 | 72.84 | 2.99 | 3.01 |
| 2.2 | 24.1925 | 5.9650 | 149.1 | 16.49 | 0.176 | 0.594 | 0 | 19.42 | 79.73 | 3.60 | 1.07 |
| 2.3 | 24.1608 | 8.3762 | 209.7 | 16.52 | 0.118 | 0.914 | 0 | 15.55 | 83.12 | 5.53 | 0.71 |
| 4.1 | 17.7698 | 1.2404 | 45.15 | 16.28 | 1.306 | 0.586 | 0 | 33.43 | 65.66 | 3.60 | 8.02 |
| 4.2 | 19.0743 | 2.0422 | 69.25 | 16.46 | 0.801 | 0.511 | 0 | 28.06 | 71.515 | 3.10 | 4.87 |
| 4.3 | 17.9379 | 2.5976 | 93.67 | 16.40 | 0.498 | 0.502 | 0 | 25.02 | 74.18 | 3.06 | 3.04 |

EXAMPLE 3

22.45 g of the upper phase mixture of paraffin-sulfonic acids after extraction as in Example 1, was mixed with 224.35 g of $CH_2Cl_2$ in a tightly sealed separator funnel. The separator funnel was thoroughly shaken and two phases were allowed to separate. After standing 24 hours at 22° C., the two separated phases were taken away from each other, and analyzed.

The lower phase was constituted by:
$H_2O$: 53.51% by weight
$H_2SO_4$: 42.48% by weight
$CH_2Cl_2$: minor amounts In the upper phase, all charged paraffin-sulfonic acids were present, together with minor amounts of $H_2O$, $H_2SO_4$, n-paraffins and $CH_2Cl_2$. In particular, the content of $H_2SO_4$, referred to the present paraffin-sulfonic acids, decreased from 18.5% by weight (before the treatment with $CH_2Cl_2$) to 6.36% by weight. Also the $H_2O$ content, still referred to the present paraffin-sulfonic acids, has decreased from 47.9% by weight to 33.0% by weight.

Aliquots of the upper phase, obtained by means of the treatment with $CH_2Cl_2$, had the composition of:
Paraffin-sulfonic acids: 5.584% by weight
($C_{12}$–$C_{18}$)-n-paraffins: 0.020% by weight
$H_2O$: 1.840% by weight
$H_2SO_4$: 0.355% by weight
$CH_2Cl_2$: the balance to 100 were extracted, inside a separator funnel, with different amounts of $H_2SO_4$ at 96% by weight at 22° C., to form a second phase or lower phase. The lower phase was constituted by $H_2SO_4$ and $H_2O$ and separated from the upper phase. The obtained values of each phase are reported in Table 3.

TABLE 3

| Test No. | $CH_2Cl_2$ Phase Charge, g | Added $H_2SO_4$ at 96%, g | Added $H_2SO_4$/paraffin-sulphonic acids % ratio, by weight | Analysis of the upper phase | | | Analysis of the lower phase | | | $H_2SO_4$/paraffin-sulphonic acids ratio in the upper phase, % by weight | $H_2O$/paraffin-sulphonic acids ratio in the upper phase, % by weight |
| --- | --- | --- | --- | --- | --- | --- | --- | --- | --- | --- | --- |
| | | | | Paraffin-sulphonic acids, % by weight | $H_2O$, % by weight | $H_2SO_4$, % by weight | Paraffin-sulphonic acids, % by weight | $H_2O$, % by weight | $H_2SO_4$, % by weight | | |
| 3.1 | 38.6158 | 1.9658 | 91.2 | 5.809 | 0.139 | 0.091 | 0 | 25.14 | 71.30 | 1.57 | 2.39 |
| 3.2 | 38.1813 | 3.7011 | 173.6 | 5.806 | 0.0317 | 0.123 | 0 | 17.84 | 79.05 | 2.12 | 0.55 |
| 3.3 | 38.2163 | 1.3300 | 62.32 | 5.720 | 0.260 | 0.106 | 0 | 29.15 | 68.00 | 1.85 | 4.55 |
| 3.4 | 38.0728 | 0.7079 | 33.30 | 5.640 | 0.491 | 0.152 | 0 | 36.63 | 61.26 | 2.70 | 8.71 |
| 3.5 | 27.9606 | 1.9132 | 122.6 | 5.804 | 0.080 | 0.142 | 0 | 21.35 | 76.47 | 2.45 | 1.38 |

EXAMPLE 4

16.1 g of the upper phase mixture of paraffin-sulfonic acids after extraction as in Example 1, was mixed with 48.6 g of $CH_2Cl_2$ in a tightly sealed separator funnel.

The separator funnel was thoroughly shaken and placed inside an oven maintained at the controlled temperature of 40° C. After 30 minutes, the separator funnel was thoroughly shaken once more inside the oven. Two phases were allowed to separate. After standing 16 hours at 40° C., the lower phase was removed, with the separator funnel being kept inside the oven. The funnel containing the upper phase was removed from the oven, and was cooled to room temperature. The two phases were analyzed.

The lower phase was constituted by:
$H_2O$: 53.47% by weight
$H_2SO_4$: 42.90% by weight
$CH_2Cl_2$: minor amounts In the upper phase, all charged paraffin-sulfonic acids were present, together with minor amounts of $H_2O$, $H_2SO_4$, n-paraffins and $CH_2Cl_2$. In particular, the content of $H_2SO_4$, referred to the present paraffin-sulfonic acids, decreased from 18.55% by weight (before the treatment with $CH_2Cl_2$) to 5.58% by weight. Also the $H_2O$ content, still referred to the present paraffin-sulfonic acids, decreased from 47.9% by weight to 27.22% by weight.

Aliquots of the upper phase, obtained by means of the treatment with $CH_2Cl_2$, had the composition of:

Paraffin-sulfonic acids: 15.98% by weight
($C_{12}$–$C_{18}$)-n-paraffins: 0.058% by weight
$H_2O$: 4.35% by weight
$H_2SO_4$: 0.892% by weight
$CH_2Cl_2$: the balance to 100 were extracted, inside a tightly sealed separator funnel that can withstand moderate pressure, with different amounts of $H_2SO_4$ at 96% by weight, by operating at 40° C. inside an oven, to form a second phase or lower phase.

After the phases separated, at 40° C., the lower phase was removed, inside the oven. The lower phase was constituted by $H_2SO_4$ and $H_2O$.

The separator was then removed from the oven, and was cooled to room temperature. The two phases were then analyzed. The values obtained for each phase are reported in Table 4.

tained at the controlled temperature of 40° C. After 1 hour, the separator funnel was thoroughly shaken once more and then left standing for 4 hours at 40° C. The lower phase (15.2294 g) was removed inside the oven. The separator containing the upper phase (143.9 g) was removed from the oven, and allowed to cool down to room temperature. The two phases were then analyzed.

The lower phase was constituted of:
$H_2O$: 25.5% by weight
$H_2SO_4$: 73.6% by weight
$CH_2Cl_2$: the balance to 100%

The lower phase did not contain paraffin-sulfonic acids.

The upper phase had the following composition:
Paraffin-sulfonic acids: 9.07% by weight
($C_{12}$–$C_{18}$)-n-paraffins: 0.033% by weight
$H_2O$: 0.230% by weight

TABLE 4

| Test No. | $CH_2Cl_2$ Phase Charge, g | Added $H_2SO_4$ at 96%, g | Added $H_2SO_4$/paraffin-sulphonic acids % ratio, by weight | Analysis of the upper phase | | | Analysis of the lower phase | | | $H_2SO_4$/paraffin-sulphonic acids ratio in the upper phase, % by weight | $H_2O$/paraffin-sulphonic acids ratio in the upper phase, % by weight |
|---|---|---|---|---|---|---|---|---|---|---|---|
| | | | | Paraffin-sulphonic acids, % by weight | $H_2O$, % by weight | $H_2SO_4$, % by weight | Paraffin-sulphonic acids, % by weight | $H_2O$, % by weight | $H_2SO_4$, % by weight | | |
| 6.1 | 11.4404 | 1.0814 | 59.2 | 17.005 | 0.860 | 0.497 | 0 | 29.71 | 69.57 | 2.92 | 5.06 |
| 6.2 | 12.7039 | 2.0280 | 99.9 | 17.090 | 0.355 | 0.447 | 0 | 24.60 | 75.7 | 2.62 | 2.08 |
| 6.3 | 10.9668 | 2.2819 | 130.2 | 16.890 | 0.243 | 0.570 | 0 | 21.32 | 78.88 | 3.37 | 1.44 |

EXAMPLE 5

23.0 g of the upper phase mixture of paraffin-sulfonic acids after extraction as in Example 1, were mixed with 142.6 g of $CH_2Cl_2$ in a tightly sealed separator funnel that can withstand moderate pressure. The separator funnel was thoroughly shaken. The separator funnel was then placed inside an oven maintained at the controlled temperature of 40° C. After 1 hour, the separator funnel was thoroughly shaken once more inside the oven. The phases were allowed to separate. After standing 26 hours at 40° C., the lower phase was removed from the interior of the oven. The funnel containing the upper phase was removed from the oven, and was allowed to cool down to room temperature. The two phases were analyzed.

The lower phase (4.4391 g) was constituted of:
$H_2O$: 56.66% by weight
$H_2SO_4$: 43.08% by weight
$CH_2Cl_2$: minor amounts In the upper phase (160.8172 g), all of the charged paraffin-sulfonic acids were present, together with minor amounts of $H_2O$, $H_2SO_4$, n-paraffins, and $CH_2Cl_2$. In particular, the content of $H_2SO_4$, referred to the present paraffin-sulfonic acids, decreased from 18.5% by weight (before the treatment with $CH_2Cl_2$) to 4.84% by weight. Also the $H_2O$ content, still referred to the present paraffin-sulfonic acids, decreased from 47.9% by weight to 28.11% by weight.

11.5 g of $H_2SO_4$ at 96% by weight was charged into a separator funnel resistant to moderate pressures, with 148.1 g of the upper phase. The separator funnel was thoroughly shaken, and placed inside an oven main- $H_2SO_4$: 0.198% by weight
$CH_2Cl_2$: the balance to 100

The $H_2SO_4$/paraffin-sulfonic acids ratio was 2.18% and the $H_2O$/paraffin-sulfonic acids ratio was 2.54%. 134 g of the upper phase was fed, in continuous mode, to a rotary evaporator operating under a slight vacuum (120–130 mm$_{Hg}$), and with the temperature of the heating bath being between 50° to 55° C. When all of the product had been fed, and approximately the total amount of $CH_2Cl_2$ has evaporated, the vacuum was increased up to 700 mm$_{Hg}$. The whole process step lasted about 1 hour.

The residual product remaining inside the kettle of the rotary evaporator after all the $CH_2Cl_2$ had evaporated, was a thin liquid essentially constituted by paraffin-sulfonic acids, with 1.585% by weight of $H_2O$, 2.182% by weight of $H_2SO_4$ and 0.360% by weight of ($C_{12}$–$C_{18}$)-n-paraffins.

The distribution of monosulfonic, disulfonic and trisulfonic acids found in the concentrated residual product resulted to be the same as found in the raw mixture of paraffin-sulfonic acids downstream from the sulfoxidation reactor.

EXAMPLE 6

By operating at 22° C., and using the same mixture of paraffin-sulfonic acids as used in Example 1, tests of purification of the paraffin-sulfonic acids from $H_2SO_4$ using different solvents, were carried out.

The results obtained are shown in Table 5. It can be observed how only the halogenated solvents supply interesting results.

TABLE 5

| Test No. | Type of solvent | Grams of solvent | Grams of paraffin-sulphonic mixture | Separated organic phase, g | Separated aqueous phase, g | Ratio, by weight, of $H_2SO_4$/paraffin-sulphonic acids in organic phase, % | Ratio, by weight, of $H_2O$/paraffin-sulphonic acids in organic phase, % | REMARKS |
|---|---|---|---|---|---|---|---|---|
| 1 | $CHCl_3$ | 3.4815 | 3.2700 | 6.0640 | 0.5247 | 4.12 | 32.2 | |

TABLE 5-continued

| Test No. | Type of solvent | Grams of solvent | Grams of paraffin-sulphonic mixture | Separated organic phase, g | Separated aqueous phase, g | Ratio, by weight, of H$_2$SO$_4$/paraffin-sulphonic acids in organic phase, % | Ratio, by weight, of H$_2$O/paraffin-sulphonic acids in organic phase, % | REMARKS |
|---|---|---|---|---|---|---|---|---|
| 2 | CCl$_4$ | 2.5884 | 3.4649 | 5.7156 | 0.3264 | 7.79 | 38.3 | |
| 3 | CH$_2$Cl—CH$_2$Cl | 3.0531 | 3.4600 | 5.1625 | 0.4214 | 10.2 | 35.4 | Also present in the intermediate phase of CH$_2$Cl—CH$_2$Cl |
| 4 | CCl$_2$=CH$_2$ | 2.6188 | 3.4609 | 5.6313 | 0.4488 | 10.99 | 33.7 | |
| 5 | (C$_2$H$_5$)$_2$O | 1.7001 | 3.3640 | 4.9189 | 0.0810 | 16.26 | 40.6 | |
| 6 | CH$_3$COOC$_2$H$_5$ | 2.3794 | 3.4308 | | | | | Single phase |
| 7 | Petroleum ether, 40–70° C. | 1.9217 | 3.3102 | | | | | Single phase |

EXAMPLE 7

7.4428 g of the upper phase mixture of paraffin-sulfonic acids after extraction as in Example 1, was mixed with 14.7382 g of CHCl$_3$ in a tightly sealed test tube. The test tube was thoroughly shaken, left standing at 23° C. for 6.5 hours, and then centrifuged to favor the phase separation of the two phases that have formed. The two phases were taken away from each other and were analyzed.

The lower phase (1.3330 g) was essentially constituted by H$_2$O (57.5% by weight) and H$_2$SO$_4$ (42.46% by weight).

The upper phase (20.7284 g), was constituted of all the charged paraffin-sulfonic acids, together with minor amounts of H$_2$O, H$_2$SO$_4$, n-paraffins, and CHCl$_3$. In particular, the content of H$_2$SO$_4$, referred to the present paraffin-sulfonic acids, decreased from 18.5% by weight (before the treatment with CHCl$_3$) to 5.74% by weight. The H$_2$O content, still referred to the present paraffin-sulfonic acids, decreased from 47.9% by weight to 29.35% by weight.

To 10.5305 g of the beforehand separated upper phase, 2.0448 g of H$_2$SO$_4$ at 96% by weight was charged. The test tube was thoroughly shaken, and was left standing at 23° C. After 7 hours, two phases formed and were taken away from each other and analyzed.

The lower phase contained H$_2$O (25.08% by weight), H$_2$SO$_4$ (73.44% by weight), together with a small amount of CHCl$_3$, and did not contain paraffin-sulfonic acids.

The upper phase had the following composition:
Paraffin-sulfonic acids: 22.75% by weight
(C$_{12}$–C$_{18}$)-n-paraffins: 0.082% by weight
H$_2$O: 0.80% by weight
H$_2$SO$_4$: 0.686% by weight
CH$_2$Cl$_2$: the balance to 100

The H$_2$SO$_4$/paraffin-sulfonic acids ratio was 3.02% and the water/paraffin-sulfonic acids ratio resulted to be 3.52%.

We claim:

1. A process for the separation of sulfuric acid from an aqueous mixture, thereof with (C$_{12}$–C$_{18}$)-paraffin-sulphonic acids, comprising the steps of:
   (a) mixing said aqueous mixture, at a temperature within the range from 10° to 80° C., with one or more halogenated solvent(s) selected from the group consisting of methane, ethane and ethylene halogenated derivatives of the general formulas of (1), (2) or (3):

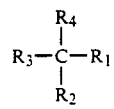

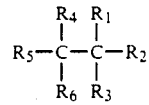

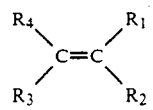

wherein at least one of R$_1$, R$_2$, R$_3$, R$_4$, R$_5$ and R$_6$ is a halogen, and the remaining R's are hydrogen, to form a two phase mixture, wherein said two phase mixture consists of an aqueous phase constituted by H$_2$SO$_4$ and H$_2$O and a residual phase containing paraffin-sulfonic acids,
   (b) mixing said residual phase with sulfuric acid to form a residual refined phase containing paraffin-sulfonic acids and a second phase, wherein said second phase is constituted by sulfuric acid in water, and
   (c) recovering paraffin-sulfonic acids by submitting said residual refined phase to a treatment of separation of the halogenated solvent or of the halogenated solvents used.

2. A process according to claim 1, wherein the halogenated solvent is selected from the group consisting of chloroform, methylene chloride, carbon tetrachloride and dichloroethane.

3. A process according to claim 1, wherein the sulfuric acid used in step (b) is mixed at a temperature between 10° to 80° C.

4. A process according to claim 3, wherein the sulfuric acid is aqueous sulfuric acid having a minimum concentration of 70% sulfuric acid.

5. A process according to claim 3, wherein the sulfuric acid is concentrated sulfuric acid.

6. A process according to claim 3, wherein the sulfuric acid is oleum.

7. A process according to claim 3, wherein the sulfuric acid is used in the form of SO$_3$.

8. A process according to claim 1, wherein the temperature in step (a) is between 20° to 50° C.

9. A process according to claim 1, wherein separation of said halogenated solvent(s) from said second phase is carried out by distillation at a temperature below about 100° C. under vaccum.

10. A process according to claim 5, wherein the sulfuric acid is 96% concentrated sulfuric acid.

11. A process according to claim 3, wherein the temperature in step (b) is from 20° to 50° C.

12. A process according to claim 1, wherein the separation of the halogenated solvent or the halogenated solvents from said residual refined phase is carried out by distillation at a temperature below about 100° C.

13. A process for the separation of sulfuric acid from an aqueous mixture thereof with ($C_{12}$–$C_{18}$)-paraffin-sulfonic acids, comprising the steps of:

(a) mixing said aqueous mixture at a temperature within the range from 10° to 80° C., with one or more halogenated solvent(s) selected from the group consisting of methane, ethane and ethylene halogenated derivatives of the general formulas of (1), (2) or (3):

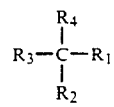

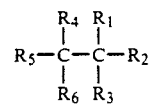

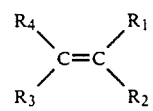

wherein at least one of $R_1$, $R_2$, $R_3$, $R_4$, $R_5$ and $R_6$ is a halogen, and the remaining R's are hydrogen and with sulfuric acid to form a residual refined phase containing paraffin sulfonic acids and a second phase, wherein said second phase is constituted by sulfuric acid in water, and (b) recovering paraffin sulfonic acids by submitting said residual refined phase to a treatment of separation of the halogenated solvent or of the halogenated solvents used.

* * * * *